United States Patent
Kutumian

(10) Patent No.: US 8,206,761 B2
(45) Date of Patent: Jun. 26, 2012

(54) MULTIPURPOSE CLEANER AND METHOD OF CLEANING USING THERAPEUTIC GRADE ESSENTIAL OILS

(76) Inventor: Dzovig M. Kutumian, Fresno, CA (US)

( * ) Notice: Subject to any disclaimer, the term of this patent is extended or adjusted under 35 U.S.C. 154(b) by 43 days.

(21) Appl. No.: 12/653,681

(22) Filed: Dec. 16, 2009

(65) Prior Publication Data

US 2011/0142970 A1 Jun. 16, 2011

(51) Int. Cl.
*A61K 36/53* (2006.01)
*A61K 36/61* (2006.01)
*A61K 36/752* (2006.01)

(52) U.S. Cl. .................. 424/736; 424/742; 424/405

(58) Field of Classification Search .................. None
See application file for complete search history.

(56) References Cited

U.S. PATENT DOCUMENTS

| | | | |
|---|---|---|---|
| 6,384,010 B1 | 5/2002 | Wagers | |
| 6,645,929 B2 | 11/2003 | Leonard et al. | |
| 6,680,074 B1 | 1/2004 | Morice | |
| 6,753,305 B2 | 6/2004 | Raso et al. | |
| 6,841,090 B1 | 1/2005 | Serego Allighieri et al. | |
| 6,884,763 B2 | 4/2005 | Willard et al. | |
| 7,741,261 B1 * | 6/2010 | Guerrero | 510/179 |
| 2008/0311215 A1 * | 12/2008 | Grace | 424/537 |

OTHER PUBLICATIONS

"House Cleaning with Essential Oils" (http://web.archive.org/web/20080517211630/http://www.aroma-essence.com/house-cleaning.html—interent archived version from May 17, 2008).*
Botanical.com (http://web.archive.org/web/20080822044258/http://www.botanical.com/products/learn/what_makes_therapeutic.html—internet archived version from Aug. 22, 2008).*
http://www.foodsubs.com/Vinegars.html—accessed Nov. 2010.*
Homemade Herbal Cleaner Recipes (http://web.archive.org/web/20080607061027/http://tipnut.com/homemade-herbal-cleaner-recipes/—internet archived version from Jun. 7, 2008).*
Horseflies website (http://web.archive.org/web/20071206042617/http://www.showhorsepromotions.com/horseflies.htm—internet archived version from Dec. 6, 2007).*
The Caldrea Company, of Minneapolis, MN, "Earth-Friendly Products", as of Dec. 13, 2009, 2 pages, at http://www.caldrea.com/AboutCaldrea.aspx?CategoryName=Our Earth Friendly Approach.

* cited by examiner

*Primary Examiner* — Susan Hoffman
(74) *Attorney, Agent, or Firm* — The Law Offices of Andrew D. Fortney; Andrew D. Fortney; Sherrie M. Flynn

(57) ABSTRACT

A multipurpose cleaning composition. The composition is a mixture of therapeutic grade essential oils, distilled white vinegar, and purified water that disinfects, degreases, and deodorizes, and also provides bioseptic and therapeutic benefits. Also provided is a method of disinfecting a surface by shaking a spray bottle having the composition, spraying the composition on the surface to be disinfected, allowing the composition to remain in contact with the surface for an amount of time sufficient to disinfect the surface, and removing the composition by wiping with a cloth. Essential oils may include, but are not limited to, therapeutic grade essential oils of eucalyptus, lemon, lavender, and grapefruit.

19 Claims, No Drawings

MULTIPURPOSE CLEANER AND METHOD OF CLEANING USING THERAPEUTIC GRADE ESSENTIAL OILS

TECHNICAL FIELD OF THE INVENTION

The invention relates to all-natural, multipurpose surface cleaners, and more particularly to all-natural, multipurpose cleaners that disinfect, degrease, and deodorize through the use of essential oils.

BACKGROUND OF THE INVENTION

The composition according to preferred embodiments of the invention is a mixture of therapeutic grade essential oils, distilled white vinegar and purified water, which serves as a multipurpose cleaner that disinfects, degreases, and deodorizes surface in, for example, homes, spas, hot tubs, vehicles, restaurants, retail stores, hotels, hospital rooms, and other private, commercial, industrial, or public locations. The composition, through a combination of therapeutic grade essential oils as active ingredients, provides therapeutic benefits in addition to its antimicrobial and biopesticide benefits.

Previously, most cleaning was performed with toxic chemicals, such as bleach, ammonia, or formaldehyde combined with solvents, emulsifiers, surfactants, preservatives and/or dyes, or with natural, biodegradable and/or environmentally friendly cleaning compositions that add essential oils to enhance the aroma, but that do not use essential oils as active ingredients. Still other natural cleaners currently known either do not provide significant disinfecting qualities or primarily utilize non-therapeutic grade essential oils, most particularly cinnamon oil, to provide disinfecting qualities, but not the therapeutic benefits of the present invention.

It is believed that therapeutic grade essential oils have not been used as the only active ingredients in a multipurpose cleaner that disinfects, degreases, deodorizes, and provides therapeutic and biopesticide benefits. There are many cleaning products that use essential oils for aroma, or use one or more essential oils as an active ingredient, but it is believe that none use therapeutic grade essential oils as their only active ingredients. See, for example, "Process for Disinfecting a Hard-Surface With a Composition Comprising Cinnamon Oil and/or An Active Thereof" by Raso, et al. (U.S. Pat. No. 6,753,305); "Cleaning Composition" by Leonard, et al. (U.S. Pat. No. 6,645,929); "All Purpose Cleaner with Low Organic Solvent Content" by Wagers (U.S. Pat. No. 6,384,010); and "Disinfecting Composition and Process for Disinfecting Surfaces" by Serego Allighieri, et al. (U.S. Pat. No. 6,841,090).

Many health-conscious consumers want cleaning products that use only natural ingredients, are environmentally friendly and safe, yet provide disinfecting and deodorizing qualities. Further, many consumers today enjoy the psychological and physical well-being derived from using therapeutic grade essential oils. Thus, there is a need for a multipurpose cleaner that disinfects, degreases, and deodorizes and, additionally, provides the therapeutic benefits derived from the use of essential oils.

SUMMARY OF THE INVENTION

To meet this and other needs, and in view of its purposes, the present invention encompasses a liquid disinfecting, degreasing, and deodorizing composition that also provides biopesticide and therapeutic benefits, comprising an effective amount of therapeutic grade essential oils, distilled white vinegar, and purified water.

Surfaces to be cleaned through use of the composition include, but are not limited to, granite, stainless steel, glass, tile, and laminate flooring. Other surfaces in homes, spas, hot tubs vehicles, restaurants, retail stores, hotels, hospital rooms, and the like may also be disinfected, degreased, and deodorized through use of the composition.

Also disclosed is a method for disinfecting a surface comprising providing effective amounts of therapeutic grade essential oils, distilled white vinegar, and purified water, shaking a spray bottle having the composition, spraying the composition on the surface to be disinfected, allowing the composition to remain in contact with the surface for an amount of time sufficient to disinfect the surface, and removing the composition from the surface by wiping with a cloth.

In a preferred embodiment of the invention, the composition comprises therapeutic grade eucalyptus essential oil, therapeutic grade lemon essential oil, therapeutic grade lavender essential oil, therapeutic grade grapefruit essential oil, and/or mixtures thereof.

A further embodiment of the invention discloses a method wherein baking soda is sprinkled on the surface to be disinfected, before applying the composition, when abrasive cleaning is required.

It is to be understood that both the foregoing general description and the following detailed description are exemplary, but are not restrictive, of the invention.

DETAILED DESCRIPTION OF THE INVENTION

The invention is a liquid disinfecting, degreasing, and deodorizing composition and a method for disinfecting surfaces using the composition that, in addition to antimicrobial benefits, also provides biopesticide and therapeutic benefits.

The Composition

The compositions of the present invention are preferably formulated as liquid compositions, with therapeutic grade essential oils comprising up to 5.0%, by volume, based on the total volume of the composition, most preferably comprising up to 3.0%, and distilled white vinegar (acetic acid in a concentration of 4% to 8% by volume) comprising up to 2.5%, by volume, based on the total volume of the composition, most preferably up to 1.5%, and purified water comprising the balance of the composition. Purified water includes, but is not limited to, distilled water, deionized water, and reverse osmosis water.

In a preferred embodiment of the invention, the therapeutic essential oils comprise essential oils of eucalyptus (*eucalyptus globules*), lemon (*citrus limonum*), lavender (*lavanula angustifolia*), and grapefruit (*citrus paradisi*). Therapeutic grade eucalyptus essential oil comprises up to 1.5%, by volume, based on the total volume of the composition, most preferably from 0.73% to 0.77%, by volume, based on the total volume of the composition. Therapeutic grade lemon essential oil comprises up to 1.5%, by volume, based on the total volume of the composition, most preferably from 0.73% to 0.77%, by volume, based on the total volume of the composition. Therapeutic grade lavender essential oil comprises up to 1.0%. by volume, based on the total volume of the composition, most preferably from 0.23% to 0.27%, by volume, based on the total volume of the composition, and therapeutic grade grapefruit essential oil comprises up to 1.0%, by volume, based on the total volume of the composition, most preferably from 0.23% to 0.27%, by volume, based on the total volume of the composition. The composition may also include any other essential oils.

The compositions of the invention have advantages over other compositions claiming disinfecting qualities because they disinfect without the use of bleach, ammonia, or formaldehyde, and without the use of solvents, emulsifiers, surfactants, preservatives and/or dyes. A further benefit of the invention is that, because it uses only therapeutic grade essential oils, it has both good disinfecting performance while providing significant therapeutic benefits.

"Effective amounts" of therapeutic grade essential oils refers to amounts that kill at least some types and number of bacteria exposed to the essential oils. "Effective amounts" of essential oils may be determined by routine testing procedures employed to evaluate effectiveness of a product at reducing specific microorganism population.

When tested, certain compositions of the present invention demonstrate excellent disinfecting performance against *pseudomonas aeruginosa* bacteria, and good disinfecting performance against *klebsiella pneumoniae* and *escherichia coli*. It was found that 100% of *pseudomonas aeruginosa* bacteria were eliminated within one minute of contact with a preferred embodiment of the invention. Additionally, 99.4% of *klebsiella pneumoniae* and 97.1% of *escherichia coli* were eliminated within five minutes of contact with a preferred embodiment of the invention. Based on a standard Time Kill/Log Reduction method of testing, it is anticipated that 100% of *klebsiella pneumoniae* and *escherichia coli* will be eliminated within seven minutes of contact with a preferred embodiment of the invention. To a lesser degree, compositions of the invention have proven effective against staphylococcus aureus. The composition may also be effective against other bacteria and contaminants.

Numerous biopesticide and therapeutic benefits are derived from the use of therapeutic grade essential oils. Therapeutic grade eucalyptus essential oil invigorates by stimulating blood flow and provides sinus and respiratory relief. It is a natural deterrent to ants and helps to rid spaces of dust mites and allergens. Therapeutic grade lemon essential oil is a natural degreaser and helps to reduce physical and mental fatigue, anxiety, nervousness, and tension. It increases concentration and improves alertness. Therapeutic grade lavender essential oil has a calming effect and helps to relieve headaches, anxiety, depression, nervous tension and emotional stress. Therapeutic grade grapefruit essential oil is a natural degreaser and helps to alleviate stress and depression. Its refreshing aroma removes nervous exhaustion and restlessness, and increases mental activity.

Other therapeutic grade essential oils provide similar and additional benefits as those described above and may include, but are not limited to, allspice oil, anise oil, basil oil, bay leaf oil, bergamot oil, camphor oil, cassia oil, cedar wood oil, chamomile oil, cinnamon oil, clove oil, geranium oil, ginger oil, hyssop oil, jasmine oil, juniper oil, lemongrass oil, lime oil, marjoram oil, nutmeg oil, orange oil, oregano oil, patchouli oil, peppermint oil, pine oil, rose oil, rosemary oil, rosewood oil, sandalwood oil, spearmint oil, tangerine oil, tea tree oil, and thyme oil.

Method of Disinfecting

The invention also encompasses methods of disinfecting surfaces with the compositions, as defined herein. A preferred method comprises the steps of shaking a spray bottle containing the composition, applying the composition to the surface to be disinfected by spraying, allowing the composition to remain in contact with the surface for an amount of time sufficient to disinfect the surface, and removing the composition from the surface by wiping with a cloth that is preferably clean. Most typically, the composition is used full-strength, but may also be diluted with water to as little as a 5.0% concentration for use, for example, when mopping tile and laminate flooring.

When abrasive cleaning is necessary, the method of disinfecting a surface may be modified to include sprinkling the surface with baking soda (sodium bicarbonate) before applying the composition by spraying.

The Summary of Invention and Detailed Description of the Invention above, and the Examples below are meant to be illustrative of particular embodiments of the invention, but are not restrictive. It is to be understood that the disclosure of the invention in this specification includes all possible combinations and equivalents thereof.

EXAMPLES

The following examples are particular embodiments of the invention and are given for illustrative purposes only. The examples are not a limitation on the scope or practice of the invention. Numerous variations of the present invention are possible without departing from the spirit and the scope of the invention, and the appended claims should not be limited to the descriptions and examples of the preferred embodiments contained herein.

The following examples are given in percentage by volume and are prepared by a simple mixing procedure:

Example 1

| Therapeutic Grade Essential Oils | 2.0% |
|---|---|
| Organic Distilled White Vinegar | 1.0% |
| Purified Water | 97.0% |

Example 2

| Therapeutic Grade Eucalyptus Essential Oil | 0.75% |
|---|---|
| Therapeutic Grade Lemon Essential Oil | 0.75% |
| Therapeutic Grade Lavender Essential Oil | 0.25% |
| Therapeutic Grade Grapefruit Essential Oil | 0.25% |
| Organic Distilled White Vinegar | 1.0% |
| Distilled Water | 97.0% |

It is expressly intended that all ranges broadly recited in this document include within their scope all narrower ranges which fall within the broader ranges.

What is claimed is:

1. A liquid disinfecting composition consisting essentially of
   amounts of therapeutic grade essential oils effective to kill at least some types and number of bacteria, including a mixture of (i) from 0.73% to 1.5% by volume of eucalyptus oil, (ii) from 0.73% to 1.5% by volume of lemon oil, (iii) from 0.23% to 1.0% by volume of lavender oil, and (iv) from 0.23% to 1.0% by volume of grapefruit oil, based on the total volume of the composition;
   up to 2.5% by volume of distilled white vinegar, and
   purified water.

2. The composition of claim 1, consisting essentially of from 1.0% to 2.5% by volume of the distilled white vinegar, based on a total volume of the composition.

3. The composition of claim 1, wherein the therapeutic grade essential oil mixture further includes one or more additional therapeutic grade essential oils selected from the group consisting of therapeutic grade allspice oil, therapeutic grade anise oil, therapeutic grade basil oil, therapeutic grade bay leaf oil, therapeutic grade bergamot oil, therapeutic grade camphor oil, therapeutic grade cassia oil, therapeutic grade cedar wood oil, therapeutic grade chamomile oil, therapeutic grade cinnamon oil, therapeutic grade clove oil, therapeutic grade geranium oil, therapeutic grade ginger oil, therapeutic grade hyssop oil, therapeutic grade jasmine oil, therapeutic grade juniper oil, therapeutic grade lemongrass oil, therapeutic grade lime oil, therapeutic grade marjoram oil, therapeutic grade nutmeg oil, therapeutic grade orange oil, therapeutic grade oregano oil, therapeutic grade patchouli oil, therapeutic grade peppermint oil, therapeutic grade pine oil, therapeutic grade rose oil, therapeutic grade rosemary oil, therapeutic grade rosewood oil, therapeutic grade sandalwood oil, therapeutic grade spearmint oil, therapeutic grade tangerine oil, therapeutic grade tea tree oil, and therapeutic grade thyme oil, and mixtures thereof.

4. The composition of claim 1, wherein the therapeutic grade essential oil mixture includes from 0.73% to 0.77% by volume of eucalyptus oil, based on a total volume of the composition.

5. The composition of claim 1, wherein the therapeutic grade essential oil mixture includes from 0.73% to 0.77% by volume of lemon oil, based on a total volume of the composition.

6. The composition of claim 1, wherein the therapeutic grade essential oil mixture includes from 0.23% to 0.27% by volume of lavender oil, based on a total volume of the composition.

7. The composition of claim 1, wherein the therapeutic grade essential oil mixture includes from 0.23% to 0.27% by volume of grapefruit oil, based on a total volume of the composition.

8. The composition of claim 1, wherein the distilled white vinegar is organic.

9. The composition of claim 1, wherein the therapeutic grade essential oils consist essentially of:
   from 0.73% to 0.77% by volume, based on a total volume of the composition, of therapeutic grade eucalyptus essential oil;
   from 0.73% to 0.77% by volume, based on the total volume of the composition, of therapeutic grade lemon essential oil;
   from 0.23% to 0.27% by volume, based on the total volume of the composition, of therapeutic grade lavender essential oil; and
   from 0.23% to 0.27% by volume, based on the total volume of the composition, of therapeutic grade grapefruit essential oil.

10. The composition of claim 1, wherein the therapeutic grade essential oils are effective to kill 100% of *Pseudomonas aeruginosa* within 1 minute, 99% of *Klebsiella pneumonia* within 5 minutes, or 97% of *Escherichia coli* within 5 minutes.

11. A method for disinfecting a surface comprising:
   shaking a spray bottle having the liquid disinfecting composition of claim 1 therein;
   spraying the composition on the surface to be disinfected;
   allowing the composition to remain in contact with the surface for an amount of time sufficient to disinfect the surface; and
   removing the composition from the surface.

12. The method of claim 11, wherein the composition consists essentially of up to 5.0% by volume of the therapeutic essential oils, based on a total volume of the composition.

13. The method of claim 11, consisting essentially of from 1.0% to 2.5% by volume of the distilled white vinegar, based on a total volume of the composition.

14. The method of claim 11, wherein the therapeutic grade essential oil mixture includes from 0.73% to 0.77% by volume of eucalyptus oil, based on a total volume of the composition.

15. The method of claim 11, wherein the therapeutic grade essential oil mixture includes from 0.73% to 0.77% by volume of lemon oil, based on a total volume of the composition.

16. The method of claim 11, wherein the therapeutic grade essential oil mixture includes from 0.23% to 0.27% by volume of lavender oil, based on a total volume of the composition.

17. The method of claim 11, wherein the therapeutic grade essential oil mixture includes from 0.23% to 0.27% by volume of grapefruit oil, based on a total volume of the composition.

18. The method of claim 11, wherein the therapeutic grade essential oils consist essentially of:
   from 0.73% to 0.77% by volume, based on a total volume of the composition, of therapeutic grade eucalyptus essential oil;
   from 0.73% to 0.77% by volume, based on the total volume of the composition, of therapeutic grade lemon essential oil;
   from 0.23% to 0.27% by volume, based on the total volume of the composition, of therapeutic grade lavender essential oil; and
   from 0.23% to 0.27% by volume, based on the total volume of the composition, of therapeutic grade grapefruit essential oil.

19. The method of claim 11 further comprising:
   sprinkling baking soda on the surface to be disinfected before spraying the composition on the surface to be disinfected.

* * * * *